United States Patent [19]
Satomura et al.

[11] Patent Number: 5,545,530
[45] Date of Patent: Aug. 13, 1996

[54] PROCESS FOR MEASURING ANALYTE IN SAMPLE

[75] Inventors: Shinji Satomura, Osaka; Kenji Nakamura, Ibaraki; Tokuji Ikenaka, Sakai; Kaoru Omichi, Toyonaka, all of Japan

[73] Assignee: Wako Pure Chemical Industries, Ltd., Osaka, Japan

[21] Appl. No.: 442,986

[22] Filed: May 17, 1995

Related U.S. Application Data

[63] Continuation of Ser. No. 860,616, Mar. 30, 1992, abandoned, which is a continuation of Ser. No. 342,044, Apr. 24, 1989, abandoned.

[30] Foreign Application Priority Data

Apr. 25, 1988 [JP] Japan .................................. 63-101798

[51] Int. Cl.$^6$ ......................... G01N 33/53; G01N 33/537
[52] U.S. Cl. .................. 435/6; 435/7.1; 435/7.9; 435/7.93; 435/803; 435/971; 436/501; 436/507; 436/536; 436/538; 436/541; 436/824; 436/512
[58] Field of Search .................. 435/6, 7.1, 7.9, 435/7.93, 803, 971; 436/501, 507, 512, 536, 538, 541, 824

[56] References Cited

U.S. PATENT DOCUMENTS

| | | | |
|---|---|---|---|
| 3,961,894 | 6/1976 | Gordon | 23/230.6 |
| 4,235,869 | 11/1980 | Schwarzberg | 436/541 |
| 4,347,058 | 8/1982 | Polito | 23/230 B |
| 4,371,515 | 2/1983 | Chu | 436/827 |
| 4,496,654 | 1/1985 | Katz | 435/7.9 |

FOREIGN PATENT DOCUMENTS

| | | |
|---|---|---|
| 0073593 | 3/1983 | European Pat. Off. . |
| 0209378 | 7/1987 | European Pat. Off. . |

OTHER PUBLICATIONS

Chemical Abstracts, vol. 104, No. 15, Apr. 14, 1986, Columbus, OH, USA, C. A. Sutheimer et al, pp. 195–196, abstract No. 124 359j & Methodol. Anal. Toxicol 1985, 3 135–46.

Chemical Abstract, vol. 89, No. 19, Nov. 6, 1978, Columbus, OH, USA, L. J. Riceberg et al, p. 260, abstract No. 159 696r & J. Pharmacol. Exp. Ther. 1978, 206(1), 158–66.

The Journal of Endocrinology, vol. 98, 1983, M. C. Stuart et al, pp. 323–330.

Journal of Immunological Methods, vol. 47, No. 2, 1981, H. A. Fields, pp. 145–159.

J. W. Freytag, Clinical Chemistry, vol. 30, No. 3, pp. 417–429 (1984).

J. W. Freytag, Clinical Chemistry, vol. 30, No. 9, pp. 1494–1498 (1984).

Schram, Steven, *The LDC Basic Book on Liquid Chromatography*, Milton Roy Co., 1980, pp. 1–69.

Holmskov–Nielsen, U., et al, *Immunology*, vol. 51, pp. 809–814 (1984).

*The LDC Basic Book of Liquid Chromatography*, Milton Roy Company, St. Petersburg, FL, pp. 101–112, 1981.

*Primary Examiner*—Toni R. Scheiner
*Attorney, Agent, or Firm*—Armstrong, Westerman, Hattori, McLeland & Naughton

[57] ABSTRACT

The amount of an analyte in a sample derived from a living sample is measured by reacting the analyte with an excess of a substance having affinity for the analyte, followed by separation of complex by high pressure liquid chromatography and measurement using a linear calibration curve representing the peak area values associated with known concentrations of analyte.

19 Claims, 5 Drawing Sheets

FIG. 1A

ELUTION TIME (min)

FIG. 1B

ELUTION TIME (min)

FIG. 2

IgG CONCENTRATION (mg/ml)

ALBUMIN CONCENTRATION (mg/ml)

FIG. 7 hCG CONCENTRATION (mIU/ml)

PROCESS FOR MEASURING ANALYTE IN SAMPLE

This application is a continuation of application Ser. No. 07/860,616 filed Mar. 30, 1992, now abandoned which was a continuation of Ser. No. 07/342,044, filed Apr. 24, 1989, now abandoned.

BACKGROUND OF THE INVENTION

This invention relates to a process for rapid, easy, and high-precision measurement of trace components in samples derived from living bodies, for example, body fluids such as serum, blood, plasma and urine, lymphocyte, hemocyte, and various cells.

It is known that specific substances interact strongly on each other (namely, they have a high affinity for each other) to form a firm complex. The specific substances include, for example, the following combinations: antigen and antibody; protease and its protein protease inhibitor; sugar chain and lectin; enzyme and substrate therefor or coenzyme; physiologically active substance such as hormone, and receptor or transport protein for said active substance; and a pair of polynucleotide chains of duplex DNA. There are widely employed methods in which trace components in samples are purified or assayed by utilizing the above interaction.

Typical examples of methods for measuring a trace component in a sample by utilizing the above interaction include a method in which an equilibrium state which results from the intereaction between an analyte to be measured and a substance having affinity for the analyte (hereinafter abbreviated as "affinity substance") is measured using a labeling substance, whereby the trace component is measured. More specific examples include radioimmunoassay (RIA), enzyme immunoassay (EIA) and fluoroimmunoassay (FIA).

In more detail, the methods for measuring trace components by measuring the equilibrium state which results from the interaction are roughly divided into the following two categories: so-called noncompetitive reaction methods which comprise reacting an affinity substance labeled with a labeling substance (hereinafter abbreviated as "labeled affinity substance") with an analyte to be measured, determining the amount of the labeling substance in the resulting complex of the analyte and the affinity substance (hereinafter abbreviated as "complex"), and thereby determining the amount of the analyte; and so-called competitive reaction methods which comprise reacting an analyte to be measured with the analyte which has been labeled with a labeling substance (hereinafter abbreviated as "labeled analyte") and an affinity substance, determining the amount of the labeling substance in the resulting complex of the labeled analyte and the affinity substance (hereinafter abbreviated as "labeled complex"), and thereby determining the amount of the analyte. The methods of each category can be further divided into so-called homogeneous methods in which measurement is carried out without separating the complex formed by the interaction from free (uncomplexed) labeled affinity substance (or labeled analyte), and so-called heterogeneous methods in which measurement is carried out after separating the complex formed by the interaction with free (uncomplexed) labeled affinity substance (or labeled analyte).

In the homogeneous method, the equilibrium state which results from the interaction is measured by utilizing the phenomenon that a labeling substance is activated (or inactivated) by the formation of the complex. Therefore, measuring procedure and the like in this method are simple, but this method is disadvantageous, for example, in that the kinds of usable labeling substance and analyte to be measured are limited. Accordingly, this method is not widely used.

In the heterogeneous method, various labeling substances can be used and substances in wide variety can be measured. Therefore, this method is a leading method for measuring a trace component. In this method, needless to say, a procedure of separating the complex (Bound form) formed by the interaction from free (uncomplexed) labeled affinity substance (or labeled analyte) (Free form), i.e., a procedure of the so-called B/F separation, is indispensable.

The B/F separation is carried out, for example, by combining the complex with an antibody against either the analyte or affinity substance constituting the complex, which has been immobilized on an insoluble carrier, and then separating the complex combined with the antibody, together with the insoluble carrier, or by adding said antibody to the reaction solution to form a new complex with said complex, and separating the thus formed complex as precipitate. Therefore, the heterogeneous method is disadvantageous, for example, in that it requires a troublesome procedure, requires a long time before measurement, and does not permit easy automation of measurement. Accordingly, its improvement is desirable.

On the other hand, in order to solve the above problems in the heterogeneous method, there have been devised methods in which the B/F separation is carried out by a so-called affinity chromatography which uses a column packed with a carrier on which an analyte to be measured or an affinity substance for the analyte has been immobilized (Clinical Chemistry, 30,417–420 (1984); Clinical Chemistry, 30, 1494–1498 (1984); etc.)

However, in these methods, free (uncomplexed) labeled affinity substance (or labeled analyte) is removed using an affinity chromatography column having the analyte (or the affinity substance) immobilized thereon. Therefore, these methods involve, for example, the following problems; the analyte (or the affinity substance) should be previously prepared (obtained) in a relatively large amount; a packing for the affinity chromatography column should be prepared; an affinity chromatography column suitable for each analyte to be measured is needed; and said column should be regenerated when a large number of samples are dealt with. Accordingly, said methods are not always satisfactory enough.

SUMMARY OF THE INVENTION

This invention was made in consideration of such conditions and is intended to provide a process which permits rapid, easy, and high-precision measurement of trace components in samples derived from living bodies, by means of the interaction between an analyte to be measured and an affinity substance.

This invention provides a process for measuring the amount of an analyte in a sample derived from a living body, which comprises mixing the sample containing an analyte to be measured with a substance having affinity for the analyte, either labeled or not with a labeling substance; reacting the analyte with the affinity substance; separating the resulting complex of the analyte and the affinity substance from free affinity substance using a high pressure liquid chromatography; and measuring the amount of the labeling substance or the amount of the affinity substance in the resulting complex.

This invention further provides a process for measuring the amount of an analyte in a sample derived from a living body, which comprises mixing the sample containing an analyte to be measured with the analyte which has been labeled with a labeling substance and a substance having affinity for the analyte; reacting the unlabeled analyte and the labeled analyte with the affinity substance; separating the resulting labeled complex of the labeled analyte and the affinity substance from free labeled analyte using a high pressure liquid chromatography; and measuring the amount of the labeling substance in the resulting complex or the amount of the labeling substance in the free labeled analyte.

DESCRIPTION OF THE PREFERRED EMBODIMENTS

The present inventors earnestly investigated a method for rapid, easy, and high-precision measurement of trace components in samples derived from living bodies, by means of the interaction between an analyte to be measured and an affinity substance. In the investigation, it was found that the separation of a complex (or a labeled complex) (Bound form) formed by said interaction from free affinity substance (or analyte to be measured) (Free form), i.e., the so-called B/F separation can easily be carried out by a high pressure liquid chromatography (HPLC) under certain conditions. It was further found that the amount of an analyte to be measured in a sample can be determined rapidly and easily with high precision by carrying out the B/F separation by HPLC, and then measuring the amount of the labeling substance or the affinity substance in the complex, or measuring the amount of the labeling substance in the labeled complex or the amount of the labeling substance in free labeled analyte.

The measuring process of this invention is practised, for example, as follows.

When the measuring process of this invention on the principle of so-called noncompetitive reaction is practised, a sample derived from a living body which contains an analyte to be measured is first reacted with a labeled or unlabeled affinity substance, if necessary, by their addition to and mixing in a suitable buffer solution, to form a complex. The complex is then separated from free affinity substance by HPLC using a column packed with a suitable packing. Subsequently, the amount of the labeling substance or the affinity substance which is contained in the complex separated is determined by a measuring method suitable for properties of the labeling substance or the affinity substance. Separately, measurement is carried out in the same manner as described above by using a sample containing a known concentration of the analyte to be measured, and there is prepared a calibration curve showing the relationship between the amount of the analyte and the amount of the labeling substance or the affinity substance in the complex. The amount of the analyte corresponding to the amount of the labeling substance or the affinity substance in the complex is determined using the calibration curve, whereby the amount of analyte in the sample can be measured.

When the measuring process of this invention on the principle of so-called competitive reaction is practiced, a sample derived from a living body which contains an analyte to be measured, labeled analyte and an affinity substance are first reacted, if necessary, by their addition to and mixing in a suitable buffer solution, to form a complex and a labeled complex. The labeled complex is then separated from free labeled analyte by HPLC using a column packed with a suitable packing. Subsequently, the amount of the labeling substance contained in the labeled complex thus separated is determined by a measuring method suitable for properties of the labeling substance. Separately, measurement is carried out in the same manner as described above by using a sample containing a known concentration of the analyte to be measured, and there is prepared a calibration curve showing the relationship between the amount of the analyte and the amount of labeling substance in the labeled complex. The amount of the analyte corresponding to the amount of labeling substance in the labeled complex is determined using the calibration curve, whereby the amount of analyte in the sample can be measured.

An analyte which can be measured by the measuring process of this invention is not critical so long as it satisfies the following condition i) or ii). i) There exists an affinity substance which can form a firm complex with the analyte by a strong interaction (affinity) between the affinity substance and the analyte, and said affinity substance can be measured (detected) in itself by some method or can be labeled with some labeling substance. ii) The analyte itself can be labeled with some labeling substance, and there exists an affinity substance which can form a firm labeled complex with the analyte by a strong interaction (affinity) between the affinity substance and the analyte. Typical examples of the analyte include proteins, peptides, nucleic acids, sugar chains, lipids, hormones, drugs, etc. which are contained in samples derived from living bodies, for example, body fluids such as serum, blood, plasma, urine and the like, lymphocytes, hemocytes, and various cells. More specific examples of the analyte include tumor markers such as α-fetoprotein (AFP), CA19-9, prostate gland specific antigen (PSA), carcinoembryonic antigen (CEA), substances having special sugar chains which cancerous cells produce; serum proteins such as immunoglobulin A (IgA), immunoglobulin E (IgE), immunoglobulin G (IgG), $\beta_2$-microglobulin, albumin, ferritin; peptides such as C-peptide, angiotensin I; enzyme proteins such as amylase, alkaline phosphates, γ-glutamyltransferase (γ-GTP); antiviral antibodies against clinically noted viruses such as rubella virus, herpesvirus, hepatitis virus, ATL virus, AIDS virus and the like; deoxyribonucleic acid (DNA) and ribonucleic acid (RNA) of pathogens such as viruses and the like, or single-stranded polynucleotides constituting nucleic acids; antigenic substances derived from pathogens such as virus and the like; antibodies reactive with allergens such as pollen of trees and plants, such as cryptomeria, indoor dust and the like; proteases such as trypsin, plasmin, serine protease, and the like; hormones such as insulin, human chorionic gonadotropin (hCG), thyroxine (T4), triiodothyronine (T3), prolactin, thyroid stimulating hormone (TSH), and the like; and drugs such as digoxin, phenytoin, morphine, nicotine, and the like.

The affinity substance according to this invention is not critical so long as it forms a firm complex with the analyte by a strong interaction (affinity) between the affinity substance and the analyte and if necessary, the affinity substance can be measured (detected) in itself by some method or can be labeled with some measurable (detectable) labeling substance (this does not apply to the case where the analyte itself can be labeled with some labeling substance). The affinity substance includes antibodies against substances having antigenicity (including haptens); antigens against antibodies; lectins having affinity for sugar chains having a specific structure, such as concanavalin A, *Lens culinaris* lectin, *Phaseolus vulgaris* lectin, *Datura stramonium* agglutinin lectin, *Triticum vulgaris* lectin, and the like; inhibitors for specific enzymes, such as $\alpha_1$-anti-trypsin for trypsin, $\alpha_2$-macroglobulin for plasmin, $\alpha_2$-macroglobulin for serine protease, and the like; and polynucleotide chains complementary to single-stranded polynucleotides which are analytes to be measured.

As the present inventive affinity substance which itself can be measured (detected) by some method, there can be exemplified, for example, substances which themselves have properties as labeling substances, such as enzymes, substances which can emit fluorescence, luminessence substances, substances which can absorb an ultraviolet light, and the like.

More specific examples of combinations of the above analytes and affinity substances are as shown in Table 1.

TABLE 1

| Analyte | Affinity substance |
| --- | --- |
| Substances having antigenecity (including haptens) | Antibodies |
| Sugar chains | Lectins |
| Inhibitors | Proteases |
| Proteases | Inhibitors |
| Antibodies | Antigen against antibodies as analytes |
| Nucleic acids | Complementary polynucleotides |

The labeling substance according to this invention includes, for example, enzymes such as alkaline phosphates, β-galactosidase, peroxidase, micro-peroxidase, glucose oxidase, glucose-6-phosphate dehydrogenase, malate dehydrogenase, luciferase, etc., which are used, for example, in EIA; radioisotopes such as $^{99m}Tc$, $^{131}I$ $^{125}I$, $^{14}C$, $^{3}H$, etc., which are used, for example, in RIA; substances which can emit fluorescence such as fluorescein, dansyl residue, fluorescamine, coumarin, naphthylamine, derivatives thereof, etc., which are used for example, in FIA; luminescent substances such as luciferin, isoluminol, luminol bis(2,4,6-trifluorophenyl) oxalate, etc.; substances which can absorb an ultraviolet light, such as phenol, naphthaol, antracene, derivatives thereof, etc.; and substances having properties such as spin, which are represented by compounds having an oxyl group, such as 4-amino-2,2,6,6-tetramethylpiperidin-1-oxyl, 3-amino-2,2,5,5-tetramethylpyrrolidin-1-oxyl, 2,6-di-t-butyl-α-(3,5-di-t-butyl-4-oxo-2,5-cyclohexadien-1-ylidene)-p-tolyloxy, etc. Needless to say, the labeling substance is not limited to these substances.

As a method for attaching the above-mentioned labeling substance to the affinity substance or the analyte to be measured, there can be exemplified all of conventional labeling methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawao "Zusetsu Keiko Kotai" 1st ed., Soft Science Inc., 1983; Eiji Ishikawa, Tadashi Kawai and Kiyoshi Miyai "Koso Men-eki Sokuteiho" 2nd ed., IGAKU-SHOIN Ltd.; R. M. Nakamura et al. "Immunoassays" Alan R. Liss. Inc., New York, 1980; and E. Harlow et al. "Antibodies" Cold Spring Harbor Laboratory, 1988). The attachment may be carried out according to these methods. Needless to say, the attachement may be carried out by a conventional method utilizing the reaction of avidin (or streptoavidin) with biotin.

In the measuring process of this invention, the reaction conditions for reacting the analyte to be measured with the labeled or unlabeled affinity substance to form a complex, or the reaction conditions for reacting the analyte to be measured with the labeled analyte and the affinity substance to form a labeled complex, are not critical so long as the reaction conditions do not inhibit the formation of the complex (or the labeled complex). The reaction may be carried out under reaction conditions employed for forming a complex in a conventional method, for example, EIA, RIA, FIA or affinity chromatography. For example, when a buffer solution is used in the reaction, as the buffer and other reagents, those used in the above conventional methods may be properly chosen.

In the measuring process of this invention which utilizes the noncompetitive reaction principle, although the concentration of the affinity substance used for forming a complex is varied depending on a value at which the limit of measurement of the analyte is set, it is usually preferable that the affinity substance is present in the reaction solution at a concentration which is not less than (preferably 2 times or more as high as, more preferably 5 times or more as high as) a concentration at which the affinity substance can find to the whole of the analyte of a concentration corresponding to the limit of measurement.

In the measuring process of this invention which utilizes the competitive reaction principle, the concentrations of the affinity substance and the labeled analyte used for forming a labeled complex are not critical and may be properly determined depending on values at which the limit of measurement of the analyte and the measurement sensitivity are set, respectively. However, needless to say, the concentration used of the labeled analyte should be not less than a concentration at which the labeled analyte can bind to the total affinity substance present in the reaction solution.

In the measuring processes of this invention, although the pH at the reaction is not critical so long as it does not inhibit the formation of the complex (or the labeled complex), it is usually 2 to 10, preferably 5 to 9. Although the temperature at the reaction is also not critical so long as it does not inhibit the formation of the complex (or the labeled complex), it is usually 0° to 50° C., preferably 20° to 40° C. As to the reaction time, since the time required for the formation of the complex (or the labeled complex) varies depending on properties of the analyte to be measured and the affinity substance, the reaction may be properly carried out for several seconds to several hours, depending on their properties.

In the HPLC used for the B/F separation in the measuring processes of this invention, any apparatus can be used without any particular problem so long as it is usually used in the analysis field and has a constant flow rate. But needless to say, as a packing used in a column for separation, various packings should be properly chosen depending on the difference in properties between the complex (or the labeled complex) and the free affinity substance (or the free labeled analyte). For example, when the molecular weight of the complex (or the labeled complex) is about 1.2 times or more, preferably 1.5 times or more, more preferably 2 times or more, the molecular weight of the affinity substance (or the labeled analyte), packings for gel filtration (gel chromatography) are suitable. When the difference between the isoelectric point of the complex (or the labeled complex) and that of the affinity substance (or the labeled analyte) is 0.05 or more, preferably 0.2 or more, packings for ion exchange chromatography or isoelectric focusing are suitable. When the complex (or the labeled complex) and the affinity substance (or the labeled analyte) are considerably different from each other in hydrophobicity, packings for hydrophobic chromatography or reversed phase chromatography are suitable. When a nucleic acid or a single-stranded polynucleotide constituting thereof is an analyte and a single-stranded polynucleotide complementary to the analyte is used as an affinity substance, hydroxyapatite or a packing for gel chromatography is used and hydroxyapatite is more preferable.

A solvent (an eluent) used for the B/F separation by HPLC is not critical so long as it neither decomposes the formed complex (or labeled complex) into the analyte (or the labeled analyte) and the affinity substance nor prevent the labeling substance contained in the complex (or the labeled complex) or the affinity substance itself from functioning as labeling substance. As the solvent, there may usually be used any of buffer solutions which are used in conventional methods such as EIA, RIA, FIA, affinity chromatography, etc. There is preferably used a buffer solution having a pH of 2 to 10 prepared by properly choosing, depending on properties of the complex (or the labeled complex) and the affinity substance (or the labeled analyte), the following materials, followed by addition and mixing: for example, buffers such as phosphates, acetates, citrates, Good's buffers, tris(hydroxymethyl)aminomethane, and the like; salts such as sodium chloride, potassium chloride, ammonium sulfate, and the like; organic solvents such as methanol, ethanol, isopropanol, acetonitrile, tetrahydrofuran, and the like; and surfactants.

In the measuring processes of this invention, the labeling substance or the affinity substance which is contained in the complex (or the labeled complex) separated by HPLC is measured by a predetermined method, depending on the kind of the labeling substance or the affinity substance. For example, when the labeling substance or the affinity substance is an enzyme, the measurement is carried out according to a conventional method of EIA, for example, any of the methods described, for instance, in Tsunehiro Kitagawa, Toshio Nanbara, Akio Tsuji, and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987; and E. Harlow et al. "Antibodies" Cold Spring Harbor Laboratory, 1988, pp. 592–598. When the labeling substance is a radioisotope, the measurement is carried out according to a conventional method of RIA by properly choosing and using a measuring instrument such as Geiger-Muller (GM) counter, liquid scintillation counter, well-type counter, counter for HPLC, or the like, depending on the kind and intensity of a radiation emitted by said radioactive substance (see, for example, Yuichi Yamamura "Ikagaku Jikken Koza Vol. 8" 1st ed., NAKAYAMA-SHOTEN Ltd. 1971; and E. Harlow et al. "Antibodies" Cold Spring Harbor Laboratory, 1988, pp. 591). When the labeling substance or the affinity substance is a substance which can emit fluorescence, the measurement is carried out according to a conventional method of FIA using a measuring instrument such as fluorometer, for example, any of the methods described in Akira Kawano "Zusetsu Keikokotai" 1st ed. Soft Science, Inc., 1983; and R. M. Nakamura et al. "Immunoassays" Alan R. Liss, Inc., New York, 1980, pp. 10. When the labeling substance or the affinity substance is a luminescent substance, the measurement is carried out according to a conventional method using a measuring instrument such as photon counter, for example, any of the methods described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 252–263, KYORITSU-SHUPPAN Ltd., published on Sep. 10, 1987; and R. M. Nakamura et al. "Immunoassays" Alan R. Liss, Inc., New York, 1980, pp. 174–176. When the labeling substance or the affinity substance is a substance which can absorb an ultraviolet light, the measurement is carried out by a conventional method using a measuring instrument such as spectrophotometer. When the labeling substance is a substance having properties as spinner, the measurement is carried out according to a conventional method using an electron spin resonance apparatus, for example, any of the methods described in Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 264–271, KYORITSU-SHUPPAN Ltd., published on Sep. 10, 1987; and R. M. Nakamura et al. "Immunoassays" Alan R. Liss. Inc., new York, 1980, pp. 213–218.

In this invention, for measuring the labeling substance or the affinity substance which is contained in the complex (or the labeled complex) separated by HPLC, there is preferably employed the method comprising introducing an effluent from a column of HPLC into a detection section as it is, and directly measuring the amount of the labeling substance or the affinity substance which is contained in the complex (or the labeled complex) in the effluent, which method is described, for example, in Shoji Hara and Akira Tsuji "Newest Liquid Chromatography" 1st ed., pp. 92–104, NANZANDO Ltd., published on Feb. 1, 1978. The reason is that this method permits rapid measurement. In this case, a reaction section of so-called post column method, in which a reagent for measuring enzyme activity is added to the effluent to react therewith, should of course be provided between the column of HPLC and the detection section. As the reagent for measuring enzyme activity which is used in the reaction section when an enzyme is used as the labeling substance or the affinity substance, there may be used a reagent prepared by a conventional method, for example, a method based on the content of Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 51–63, KYORITSU-SHUPPAN Ltd., published on Sep. 10, 1987; E. Harlow et al. "Antibodies" Cold Spring Harbor Laboratory, 1988, pp. 592–598; or R. M. Nakamura et al. "immunoassays" Alan R. Liss, Inc., New York, 1980, or there may be properly chosen and used a reagent of a commercially available kit for clinical examination. Also when the labeling substance or the affinity substance is other than enzyme, a suitable reaction section may be used between the column of HPLC and the detection section in order to add and react a predetermined reagent for the purpose of increasing the detection sensitivity.

In the present invention measuring process on the noncompetitive reaction principle, when an antibody is used as the affinity substance, it is preferable to use the antibody after digesting it properly with an enzyme such as pepsin or papain into F(ab')$_2$, Fab' or Fab, depending on purposes. The reason is as follows. Immunoglobulin contained as antibody in usual antiserum is usually of IgG class. The molecular weight of IgG is about 150,000 and that of peroxidase-labeled IgG is about 200,000. When a peroxidase-labeled complex obtained by the reaction of peroxidase-labeled IgG with an analyte to be measured and free peroxidase-labeled IgG are subjected to B/F separation on the gel chromatography principle, the separation is difficult unless the molecular weight of the analyte is about 50,000 or more, and therefore the kind of the analyte is inevitably limited. When an antibody to be used is digested with an enzyme into F(ab')$_2$ (molecular weight: about 100,000), Fab' (molecular weight: about 50,000) or Fab (molecular weight: about 50,000) and there is used a labeled affinity substance obtained by attaching a labeling substance to the digestion product, a substance having a molecular weight of about 10,000 or more can be desirably used as analyte to be measured. Needless to say, when Fab' or Fab is used for the purpose described above, the molecular weight of the labeling substance is preferably as low as possible. For example, when an enzyme is used as the labeling substance, a low-molecular-weight enzyme such as micro-peroxidase (molecular weight: about 1800) is preferable. In the case of using a monoclonal antibody having a property of binding only to one epitope site, when a product obtained by attaching a labeling substance to Fab' or Fab obtained by digesting the monoclonal antibody is used as the affinity substance, the labeling substance can be attached to an analyte to be measured, in a proportion of 1 molecule per molecule of the analyte (or 1 molecule per molecule of monomer in the case where the analyte is a dimer, a trimer or the like), so that the linearity of a calibration curve for measurement is improved. Therefore, employment of said product is more preferable.

Also in the measuring process on the competitive reaction principle, when an antibody is used as the affinity substance, it is preferable to use the antibody after digesting it properly with an enzyme such as pepsin or papain into F(ab')$_2$, Fab' or Fab, depending on purposes. Particularly in the case of using a monoclonal antibody having a property of binding only to one epitope site, when Fab' or Fab obtained by digesting the monoclonal antibody is used as the affinity substance, the affinity substance can be bound to the unlabeled analyte or the labeled analyte in a proportion of 1 molecule per molecule each of the unlabeled analyte or the labeled analyte (or in a proportion of 1 molecule per molecule of monomer in the case where the analyte to be measured is a dimer, a trimer or the like), and hence properties such as molecular weight, isoelectric point and the like of the labeled complex become constant, so that the separation becomes easy. Therefore, the employment of Fab' or Fab is preferable.

Needless to say, in the measuring processes of this invention, the amount of analyte can be measured not only by measuring the amount of the labeling substance or the affinity substance in the complex (or the labeling substance in the labeled complex) formed by the interaction, but also by measuring the amount of the labeling substance in free labeled affinity substance which has not participated in the formation of the complex, or the amount of free affinity substance, or by measuring the amount of the labeling substance in free labeled analyte.

As the antibody used as affinity substance in this invention, there may be used either polyclonal antibodies prepared by immunizing animals such as horse, cattle, sheep, rabbit, goat, rat, mouse, etc. with an analyte to be measured, according to a conventional method, for example, any of the methods described in Tadashi Matsuhashi et al. "Menekigaku Jikken Nyumon" 2nd ed., GAKKAI-SHUPPAN CENTER Ltd., 1981; and E. Harlow et al. "Antibodies" Cold Spring Harbor Laboratory, 1988, pp. 53–138, or monoclonal antibodies produced by Hybridomas obtained by fusing cells from a tumor line of mouse together with mouse spleen cells previously immunized with an analyte to be measured, according to the conventional method, i.e., the cell fusion method established by G. Köhler and C. Milstein (Nature, 256,495, 1975). These polyclonal and/or monoclonal antibodies may be used singly or in proper combination of two or more thereof.

In the processes of this invention, for forming the complex (or the labeled complex), there are, if necessary, employed two or more affinity substances (specifically, two or more affinity substances which bind to different sites, respectively, on the analyte to be measured). This employment results in a higher molecular weight of the complex (or the labeled complex) and variation of its isoelectric point. Therefore, the separation of the complex (or the labeled complex) from free affinity substances (or free labeled analyte) becomes more easy, so that the precision of measurement can be improved. Furthermore, the measurement sensitivity, of course, can be increased by attaching a labeling substance to each affinity substance.

In the measuring process on the noncompetitive reaction principle, the measurement sensitivity may be controlled by combined use of labeled affinity substance and unlabeled one. When the reaction is carried out by the combined use of them, the analyte to be measured reacts with both the labeled affinity substance and the unlabeled one to form a complex containing the labeling substance and a complex containing no labeling substance. The ratio of the former complex to the latter complex is proportional to the ratio of the labeled affinity substance to the unlabeled one at the time of reaction. Therefore, the measurement sensitivity can be controlled when the proportion of the complex containing the labeling substance is varied by varying the proportion of the unlabeled affinity substance, and the analyte to be measured is measured by determining the amount of the labeling substance in the complex. In this case, although the labeled affinity substance and the unlabeled affinity substance are usually derived from the same affinity substance, they may, of course, be different in the kind of affinity substance so long as they are such that when one of them binds to the analyte to be measured, the other cannot bind thereto.

In the case where the combination of an analyte to be measured and an affinity substance is a combination of antigen and antibody, when the analyte is measured by a conventional method such as an EIA method or an RIA method, at least, several hours, in some cases, several days, are required for obtaining a measurement result. According to the process of this invention, the time required for the measurement is usually as very short as several tens of minutes. This is quite unexpected fact which contradicts customary ideas as to antigen-antibody reaction.

This invention is more concretely explained below with reference to Examples, which are not by way of limitation but by way of illustration.

EXAMPLE 1

Measurement of immunoglobulin G (IgG)

Eluent

An eluent was prepared by dissolving 13.0 g of monosodium phosphate, 59.7 g of disodium phosphate, 48.3 g of sodium chloride and 5 g of sodium azide in deionized water to make a total volume of 5 liters.

Samples

Solutions having a human IgG concentration of 0.60, 0.48, 0.36, 0.24, 0.12 or 0.06 mg/ml were prepared as samples by dissolving human IgG (available from Sigma Chemical Co.) in physiological saline.

Antibody solution

A solution having an antibody protein concentration of 10 mg/ml was prepared as an antibody solution by adding anti-human IgG (mouse) monoclonal antibody (available from Wako Pure Chemical Industries, Ltd.) to the aforesaid eluent.

Use conditions of HPLC

Column: 1 cm in diameter×30 cm

Packing: TSK gel G-3000 SW a hydrophilic silica gel (a trade name, Tosoh Ltd.)

Flow rate: 0.8 ml/min

Detection: Absorbance at 280 nm was measured.

Measuring procedure

With 150 μl of the antibody solution was mixed 100 μl of each sample at room temperature, and 50 μl of the resulting mixture was analyzed by HPLC.

Results

Figure 1A:
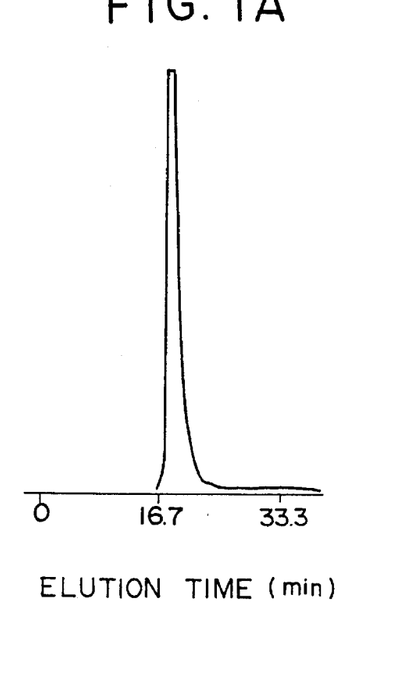
FIGS. 1A and 1B show an elution pattern of a sample which was obtained by a high pressure liquid chromatography (HPLC) in Example 1.
Figure 1B:
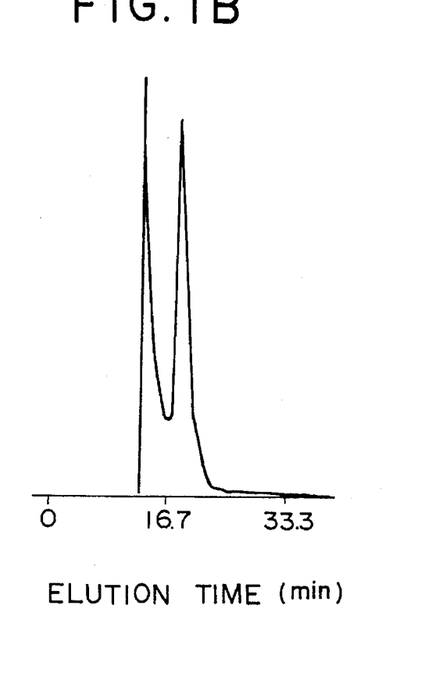

The elution pattern obtained is shown in FIG. 1. In FIG. 1, A shows an analysis result obtained when physiological saline was reacted in place of the sample, and B that obtained when the sample containing 0.60 mg/ml of human IgG was used.

It can be seen that as is clear from FIG. 1, when a complex is formed by the antigen-antibody reaction, the complex is separated from free antibody by HPLC.

Figure 2:
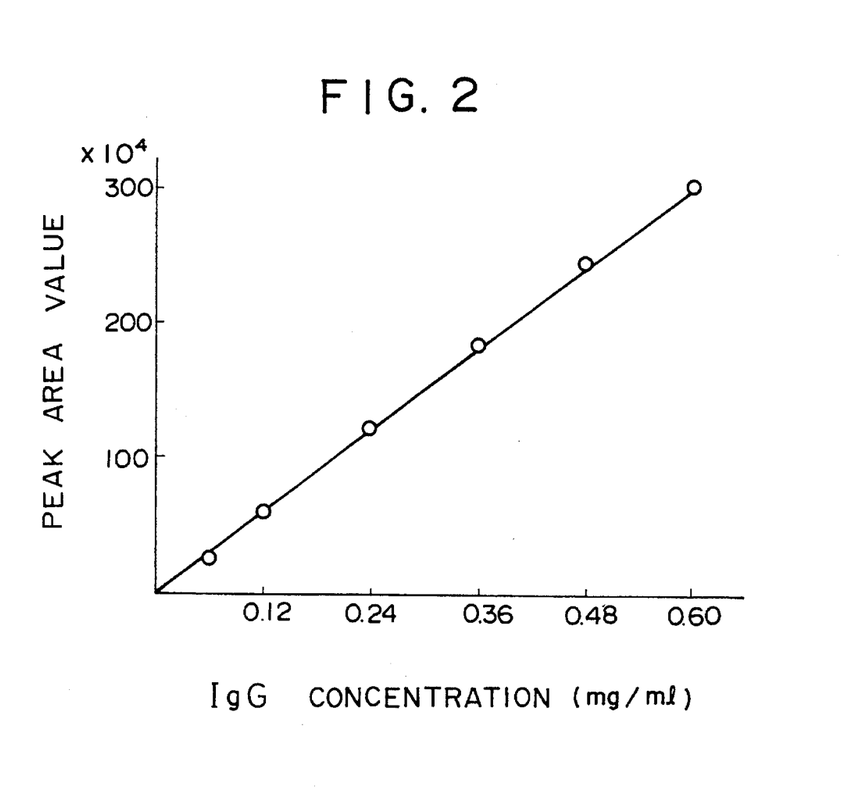
FIG. 2 shows a calibration curve for IgG which was obtained in Example 1.

In FIG. 2 is shown a calibration curve showing the relationship between the human IgG concentration of each sample and the peak area value of the complex which was obtained by the analysis.

As is clear from FIG. 2, the calibration curve showed good linearity.

EXAMPLE 2

Measurement of immunoglobulin E (IgE)

Eluent

An eluent was prepared by dissolving 60 g of tris(hydroxymethyl)aminomethane in 8 liters of deionized water, adjusting the resulting solution to pH 8.5 with acetic acid, and then making up the total volume of 10 liters.

Substrate solution

A substrate solution was prepared by dissolving 16.6 g of 3-(p-hydroxyphenyl)-propionic acid and 630 mg (220 mg in terms of $H_2O_2$) of a 35% aqueous hydrogen peroxide solution in the aforesaid eluent to make a total volume of 1 liter.

Antibody solution

An antibody solution was prepared by treating anti-human IgE (mouse) monoclonal antibody (available from Wako Pure Chemical Industries, Ltd.) into Fab' by a conventional method, labeling this Fab' with horseradish peroxidase (POD) by a conventional method, and adding the thus obtained POD-labeled anti-human IgZ-Fab' to the aforesaid eluent to adjust the protein concentration to 0.5 mg/ml.

Samples

Solutions having an IgE concentration of 62, 125, 250, 500 or 1,000 U/ml were prepared as samples by diluting commercially available IgE standard serum (available from Hoechst AG) with physiological saline.

Use conditions of HPLC

Figure 3:
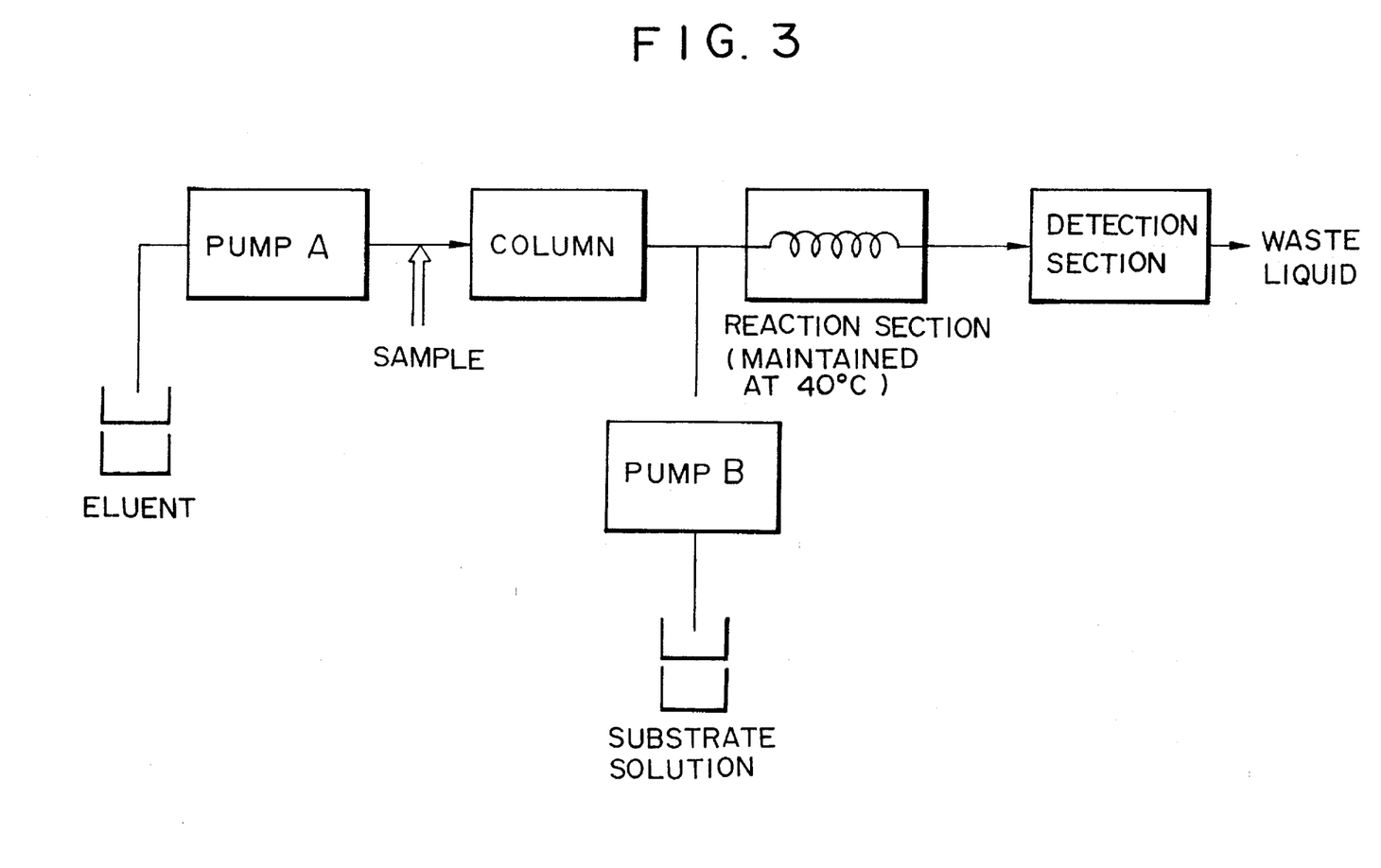
FIG. 3 is a schematic diagram of the system of HPLC used in Examples 2, 4, 5, 6, 7, 8 and 9.

The outline of a system is given in FIG. 3.

Column: 1 cm in diameter (φ)×30 cm

Packing: SUPEROSE 12 an agarose gel (a trade name, Pharmacia AB).

Flow rate: the eluent; 0.8 ml/min, the substrate solution; 0.2 ml/min.

Detection: Fluorescence was measured at an excitation wavelength of 320 nm and an emission wavelength of 404 nm.

Measuring procedure

With 150 μl of the antibody solution was mixed 100 μl of each sample at room temperature, and 5 μl of the resulting mixture was analyzed by HPLC.

Results

As a result of the analysis by HPLC, it was found that the retention time of POD-labeled anti-human IgE-Fab' was 19.2 minutes and that of complex of IgE and the POD-labeled anti-human IgE-Fab' was 15.6 minutes.

Figure 4:
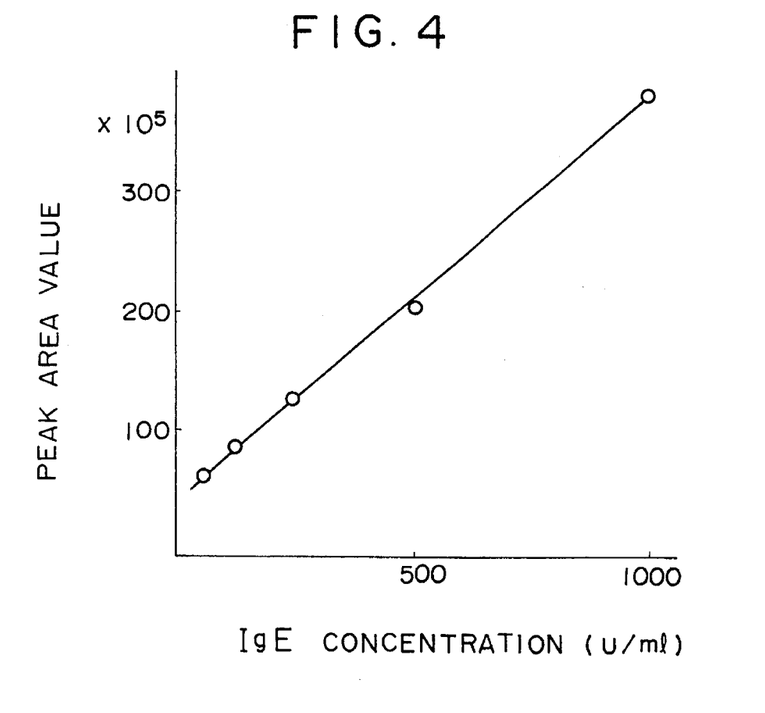
FIG. 4 shows a calibration curve for immunoglobulin E (IgE) which was obtained in Example 2.

In FIG. 4 is shown a calibration curve showing the relationship between the human IgE concentration of each sample and the peak area value of the complex which was obtained by the analysis.

As is clear from FIG. 4, the calibration curve showed good linearity.

EXAMPLE 3

Measurement of immunoglobulin A (IgA)

Eluent

An eluent was prepared by dissolving 2.3 g of monopotassium phosphate, 11.9 g of disodium phosphate dodecahydrate and 8.8 g of sodium chloride in deionized water to make a total volume of 1,000 ml.

Antibody solution

An antibody solution was prepared by adding anti-human IgA (α) (goat) FITC-labeled antibody (available from Litton Bionetics, Inc.) to the aforesaid eluent to adjust the protein concentration to 0.8 mg/ml.

Samples

Solutions having a human IgA concentration of 0.012, 0.024, 0.036, 0.048 or 0.060 mg/ml were prepared as samples by dissolving human IgA (available from Jackson Immuno Research Laboratories Inc.) in physiological saline.

Use conditions of HPLC

Column: 1 cm in diameter×30 cm
Packing: SUPEROSE 12 (a trade name, Pharmacia AB)
Flow rate: 0.8 ml/min
Detection: Fluorescence was measured at an excitation wavelength of 495 nm and an emission wavelength of 525 nm.

Measuring procedure

With 50 μl of the antibody solution was mixed 50 μl of each sample at room temperature, and 50 μl of the resulting mixture was analyzed by HPLC.

Results

As a result of the analysis by HPLC, it was found that anti-human IgA (α) (goat) FITC-labeled antibody was eluted after 17.7 minutes and a complex of IgA and anti-human IgA (α) (goat) FITC-labeled antibody after 13.0 minutes.

Figure 5:
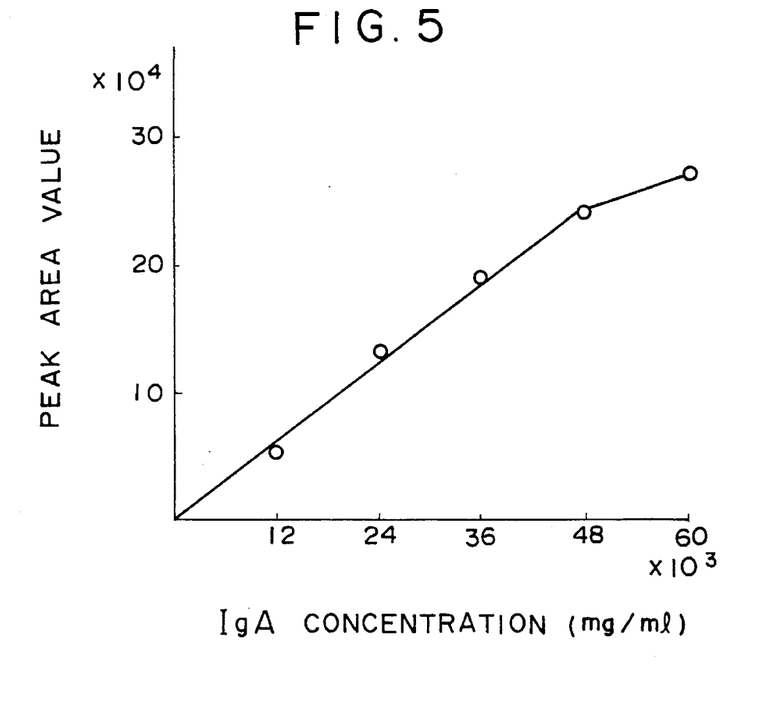
FIG. 5 shows a calibration curve for immunoglobulin A (IgA) which was obtained in Example 3.

In FIG. 5 is shown a calibration curve showing the relationship between the human IgA concentration of each sample and the peak area value of the complex which was obtained by the analysis.

As is clear from FIG. 5, the calibration curve showed good linearity.

EXAMPLE 4

Measurement of albumin

Eluent

An eluent was prepared by dissolving 23 g of monopotassium phosphate and 119 g of disodium phosphate dodecahydrate in deionized water to make a total volume of 10 liters.

Substrate solution

A substrate solution was prepared by dissolving 6.43 g of 2,2'-azino-bis(3-ethylbenzothiazoline-6-sulfonic acid) and 2430 mg (850 mg in terms of $H_2O_2$) of a 35% aqueous hydrogen peroxide solution in the aforesaid eluent to make a total volume of 1 liter.

Antibody solution

Each of anti-human albumin (mouse) monoclonal antibodies A and B (hereinafter abbreviated as AAM-A and AAM-B, respectively: their respective antigen-recognition sites are different from each other) obtained by culturing each of two clones of mouse hybridoma producing anti-human albumin antibody which has been prepared by a conventional method, was made into Fab' by a conventional method. These Fab's were labeled with POD, and the thus obtained POD-labeled AAM-A and POD-labeled AAM-B were added to the aforesaid eluent to adjust the concentration of each protein to 2 mg/ml, whereby an antibody solution was obtained.

Samples

Solutions having a human albumin concentration of 0.005, 0.01, 0.02 or 0.04 mg/ml were prepared as samples by dissolving human albumin (available from Wako Pure Chemical Industries, Ltd.) in physiological saline.

Use conditions of HPLC

The outline of a system was as given in FIG. 3.
Column: 1φ×30 cm
Packing: SUPEROSE 6 an agarose gel (a trade name, Pharmacia AB).
Flow rate: the eluent; 0.6 ml/min, the substrate solution; 0.15 ml/min.
Detection: Absorbance at 405 nm was measured.

Measuring procedure

With 100 μl of the antibody solution was mixed 50 μl of each sample, and after standing at 37° C. for 10 minutes, 5 μl of the mixture was analyzed by HPLC.

Results

As a result of the analysis by HPLC, it was found that both POD-labeled AAM-A and POD-labeled AAM-B were eluted after 25 minutes and a complex of both POD-labeled AAM-A and POD-labeled AAM-B and human albumin was eluted after 22 minutes.

Figure 6:
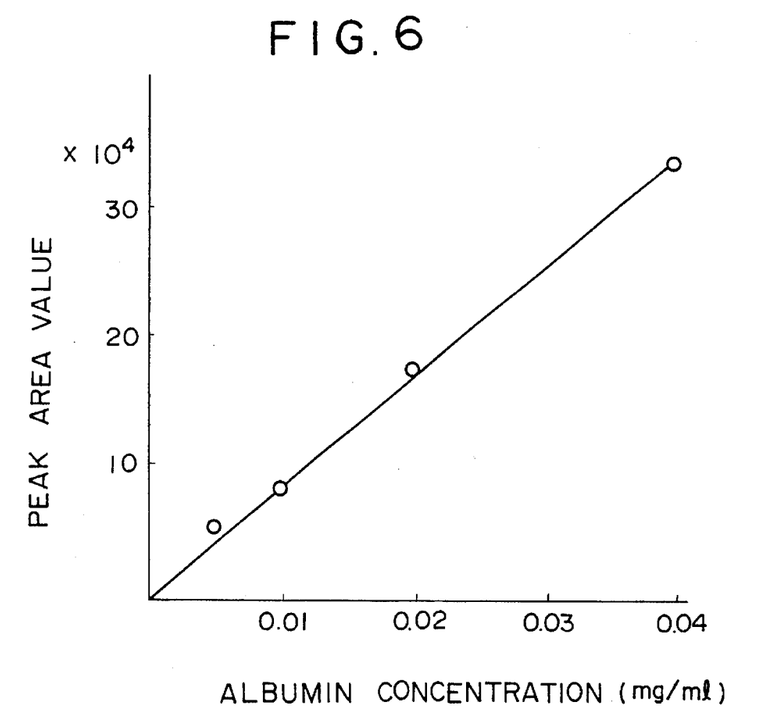
FIG. 6 shows a calibration curve for human albumin which was obtained in Example 4.

In FIG. 6 is shown a calibration curve showing the relationship between the human albumin concentration of each sample and the peak area value of the complex which was obtained by the analysis.

As is clear from FIG. 6, the calibration curve showed good linearity.

When the same reaction as described above was carried out using only either POD-labeled AAM-A or POD-labeled AAM-B as a POD-labeled antibody, a complex of the POD-labeled antibody and human albumin could not be sufficiently separated from free POD-labeled antibody. It is conjectured that this is because the difference in molecular weight between the complex of albumin and only either POD-labeled AAM-A or POD-labeled AAM-B and POD-labeled AAM-A or POD-labeled AAM-B, respectively, was too small to separate the complex from free POD-labeled antibody sufficiently.

EXAMPLE 5

Measurement of human chorionic gonadotropin (hCG)

Eluent

An eluent (pH 7.0) was prepared by dissolving 3.9 g of monosodium phosphate, 81 g of disodium phosphate dodecahydrate, 44 g of sodium chloride and 8.3 g of 3-(p-hydroxyphenyl)-propionic acid in deionized water to make a total volume of 5 liters.

Substrate solution

A 20 mM solution of $H_2O_2$ was prepared as a substrate solution by diluting a 30% aqueous hydrogen peroxide solution with deionized water.

Antibody solution 1

Anti-hCG-β chain polyclonal antibody (rabbit) (formed using the C-terminal peptide of hCG-β chain as antigen: available from Wako Pure Chemical Industries, Ltd.) was treated into Fab' by a conventional method. This Fab' was labeled with horseradish peroxidase (POD) by a conventional method and the thus obtained POD-labeled anti-hCG-β chain-Fab' was added to 50 mM phosphate buffer (pH 7.0, containing 150 mM sodium chloride) to adjust the protein concentration to 950 µg/ml, whereby antibody solution 1 was obtained.

Antibody solution 2

Antibody solution 2 was prepared by adding anti-hCG-β chain monoclonal antibody (mouse) (different in epitope from the antibody used in antibody solution 1: available from Wako Pure Chemical Industries, Ltd.) to 50 mM phosphate buffer (pH 7.0, containing 150 mM sodium chloride) to adjust the protein concentration to 500 µg/ml.

Samples

Solutions having a hCG concentration of 100, 200, 300, 400 or 500 mIU/ml were prepared as samples by dissolving commercially available hCG (available from Sigma Chemical Co.) in deionized water.

Use conditions of HPLC

The outline of a system was as given in FIG. 3.

Column and packing: 0.8φ×30 cm, YMC-Diol-200, a diol containing silica gel (a trade name, Yamamura Chemical Laboratories Co., Ltd.).

Flow rate: the eluent; 1.0 ml/min, the substrate solution; 0.1 ml/min.

Detection: Fluorescence was measured at an excitation wavelength of 320 nm and an emission wavelength of 404 nm.

Measuring procedure

After 40 µl of antibody solution 1, 40 µl of antibody solution 2 and 50 µl of each sample were mixed at room temperature, 100 µl of the mixture was analyzed by HPLC.

Results

Figure 7:
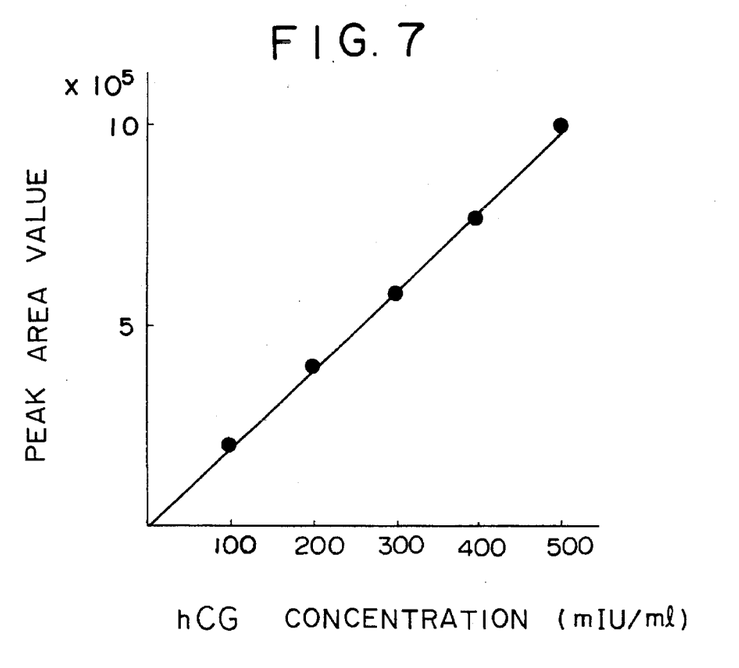
FIG. 7 shows a calibration curve for human chorionic gonadotropin (hCG) which was obtained in Example 5.

In FIG. 7 is shown a calibration curve showing the relationship between the hCG concentration of each sample and the peak area value of complex, which was obtained as a result of the analysis by HPLC.

As is clear from FIG. 7, the calibration curve showed good linearity.

As a result of the analysis by HPLC, it was found that the POD-labeled anti-hCG-β chain-Fab' was eluted after 12.0 minutes, a complex of the POD-labeled anti-hCG-β chain-Fab' and human hCG after 9.5 minutes, and a complex of the POD-labeled anti-hCG-β chain-Fab', anti-hCG-β chain (mouse) monoclonal antibody and hCG after 8.2 minutes. It can be seen that as is clear from these results, the separation of the complex of hCG, the POD-labeled anti-hCG-β chain-Fab' and anti-hCG-β chain (mouse) monoclonal antibody from free POD-labeled anti-hCG-β chain-Fab' can be conducted more certainly than the separation of the complex of hCG and the POD-labeled anti-hCG-β chain-Fab' from free POD-labeled anti-hCG-β chain-Fab'.

EXAMPLE 6

Measurement of human α-fetoprotein (AFP)

Eluent

An eluent (pH 7.0) was prepared by dissolving 3.9 g of monosodium phosphate, 81 g of disodium phosphate dodecahydrate, 44 g of sodium chloride and 8.3 g of 3-(p-hydroxyphenyl)-propionic acid in deionized water to make a total volume of 5 liters.

Substrate solution

A 20 mM solution of $H_2O_2$ was prepared as a substrate solution by diluting a 30% aqueous hydrogen peroxide solution with deionized water.

Antibody solution 1

Anti-AFP (mouse) monoclonal antibody (available from TAKARA SHUZO CO., Ltd.) was treated into Fab' by a conventional method. This Fab' was labeled with horseradish peroxidase (POD) by a conventional method. The thus obtained POD-labeled anti-AFP-Fab' added to 50 mM phosphate buffer (pH 7.0, containing 150 mM sodium chloride) to adjust the protein concentration to 10 µg/ml, whereby antibody solution 1 was obtained.

Antibody solution 2

Antibody solution 2 was prepared by adding the same monoclonal antibody as used in antibody solution 1 to 50 mM phosphate buffer (pH 7.0, containing 150 mM sodium chloride) to adjust the protein concentration to 50 ng/ml.

Samples

Solutions having an AFP concentration of 200, 400, 600, 800 or 1,000 ng/ml were prepared as samples by dissolving commercially available AFP (available from DAKOPATTS, Denmark) in 50 mM phosphate buffer (pH 7.0, containing 150 mM sodium chloride).

Use conditions of HPLC

The outline of a system was as given in FIG. 3.

Column and packing: 0.8φ×30 cm, YMC-Diol-300 (a trade name, Yamamura Chemical Laboratories Co., Ltd. ).

Flow rate: the eluent; 1.0 ml/min, the substrate solution; 0.1 ml/min.

Detection: Fluorescence was measured at an excitation wavelength of 320 nm and an emission wavelength of 404 nm.

Measuring procedure 1

With 40 µl of antibody solution 1 was mixed 40 µl of antibody solution 2 at room temperature, after which 50 µl of each sample was mixed therewith at room temperature and 100 µl of the resulting mixture was analyzed by HPLC.

Measuring procedure 2

After 40 μl of antibody solution 1, 40 μl of 50 mM phosphate buffer (pH 7.0, containing 150 mM sodium chloride) and 50 μl of each sample were mixed at room temperature, 100 μl of the resulting mixture was analyzed by HPLC.

Results

Figure 8:
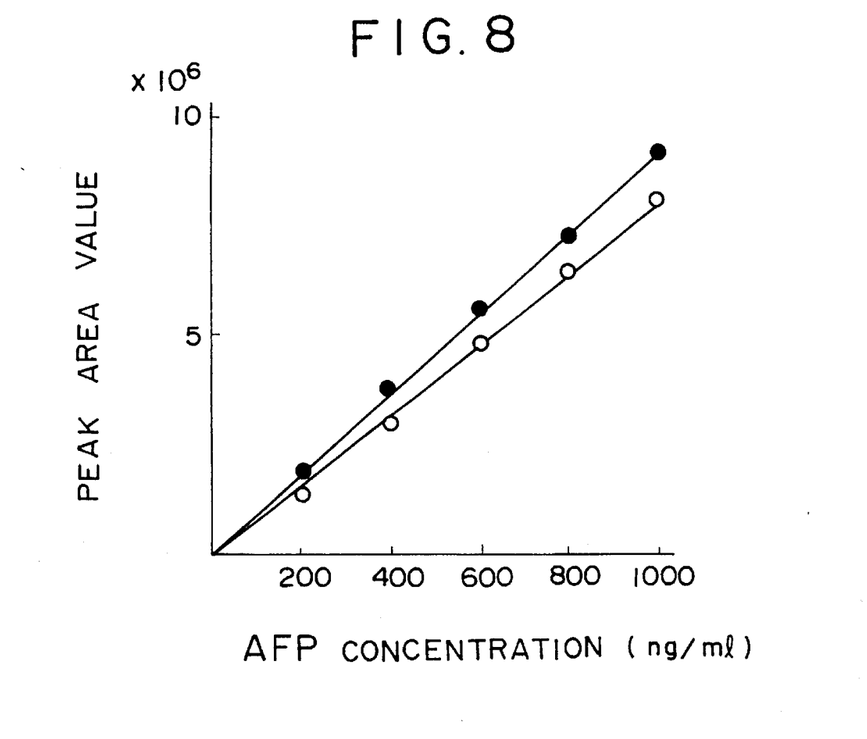
FIG. 8 shows a calibration curve for human α-fetoprotein (AFP) which was obtained in Example 6.

In FIG. 8 is shown calibration curves showing the relationship between the AFP concentration of each sample and the peak area value of complex, which were obtained as a result of the analysis by HPLC. In FIG. 8, —o— shows the results obtained by measuring procedure 1 and —●— those obtained by measuring procedure 2.

As is clear from FIG. 8, although the peak area value of complex, namely, the measurement sensitivity, was different in the measuring procedure, both calibration curves showed good linearity. This results indicated that the measurement sensitivity can be controlled by use of antibody solution 2, namely, that the measurement sensitivity can be controlled by adding the unlabeled affinity substance used for preparing the labeled affinity substance.

EXAMPLE 7

Measurement of hepatitis virus B (HBs) DNA

Eluent 1

Eluent 1 was prepared by dissolving 1.6 g of monosodium phosphate and 1.6 g of 3-(p-hydroxyphenyl)-propionic acid in 500 ml of deionized water, adjusting the pH of the resulting solution to 6.7 with a 1N aqueous sodium hydroxide solution, and then making up the solution to 1 liter with deionized water.

Eluent 2

Eluent 2 was prepared by dissolving 78 g of monosodium phosphate and 1.6 g of 3-(p-hydroxyphenyl)-propionic acid in 500 ml of deionized water, adjusting the pH of the resulting solution to 6.7 with a 1N aqueous sodium hydroxide solution, and then making up the solution to 1 liter with deionized water.

Substrate solution

A 20 mM solution of $H_2O_2$ was prepared as a substrate solution by diluting a 30% aqueous hydrogen peroxide solution with deionized water.

Labeled oligonucleotide probe solution i) Preparation of an oligonucleotide probe By the β-cyanoethyl phosphoamidite method, there were carried out synthesis of 5'-CTTCTGGATTATCAAGG-TATGT-3' (wherein A, G, C and T denote base residues of adenine, guanine, cytosine and thymine, respectively) which is a part of a base sequence coding for adw type HBsAg gene, and addition of β-link thiol linker (Biosearch Inc.) to the 5'-terminal. Deprotection, SH group activation and purification were carried out by conventional methods.

ii) Labeling of the oligonucleotide probe with POD

To 300 μl of a POD solution (7 mg/ml in 0.1M phosphate buffer, pH 7.0) was added 1 mg of sulfosuccinimidyl-4-(N-maleimidomethyl)cyclohexane-1-carboxylate (mfd. by Pierce Chemical Co.), and the resulting solution was incubated at 30° C. for 1 hour. The POD derivative was purified using a SEPHADEX, G-25, an agarose gel (Pharmacia AB) equilibrated with 20 mM phosphate buffer (containing 150 mM sodium chloride, pH 7.0), and a fraction containing POD was collected and the concentrated by ultrafiltration. To the concentrate was added 100 μg of the oligonucleotide obtained in i) above (the SH group had been activated), and the resulting mixture was allowed to stand at 4° C. for 20 hours. The mixture was then subjected to purification by a column chromatography using DEAE-trisacryl (mfd. by Wako Pure Chemical Industries, Ltd.) to obtain 140 μg of a POD-labeled oligonucleotide probe.

iii) Labeled oligonucleotide probe solution

The POD-labeled oligonucleotide probe obtained in ii) above was dissolved in 1.8 nM phosphate buffer (pH 7.4, containing 0.75M sodium chloride, 4.5 mM EDTA, 0.1% Ficoll, 0.1% Polyvinylpyrroldone, 3.0% bovine serum albumin and 0.5% TRITON X-100) in a concentration of 100 ng/ml to obtain a labeled oligonucleotide probe solution.

Sample pHBV 933 (7.6 Kb) was prepared by inserting adw type HBV genome (3.2 Kb) in pBR 322 vector (4.4 Kb) in its EcoR I site by the method of Ono et al. (Nucleic Acids Research, 11, 1747–1757, 1983). The thus obtained pHBV 933 was cleaved using a restriction enzyme Sal I to obtain a linear product. An aqueous solution of the linear product having a concentration of 10 ng/ml was used as a sample.

Use conditions of HPLC

The outline of a system was as given in FIG. 3.

Column and packing: 0.57 φ×7.5 cm, TSK gel HA 1000 (a trade name, Tosoh Ltd.).

Flow rate: the eluents; 1.0 ml/min, the substrate solution; 0.1 ml/min.

Detection: Fluorescence was measured at an excitation wavelength of 320 nm and an emission wavelength of 404 nm.

measuring procedure

After 100 μl of the sample was heat-treated at 95° C. for 10 minutes and then ice-cooled, 100 μl of the labeled oligonucleotide probe solution was added. The resulting mixture was incubated at 37° C. for 30 minutes, after which 50 μl of the mixture was analyzed by HPLC.

In the analysis by HPLC, gradient elution was carried out using eluent 1 and eluent 2. In detail, from 0 to 5 minutes after the injection, elution was carried out using eluent 1 alone. From 5 to 35 minutes, elution was carried out while increasing the percentage of eluent 2 from 0 to 100% with a linear gradient. From 35 to 40 minutes, elution was carried out using eluent 2 alone.

Results

As a result of the analysis by HPLC, it was found that the POD-labeled oligonucleotide probe was eluted after 5.0 minutes and a complex of the POD-labeled oligonucleotide probe and the hepatitis virus B DNA after 9.8 minutes. This result indicates that HBs DNA can be detected by the process of this invention.

EXAMPLE 8

Measurement of HBs DNA (2)

Eluent

An eluent (pH 7.0) was prepared by dissolving 3.9 g of monosodium phosphate, 81 g of disodium phosphate dodecahydrate, 147 g of sodium chloride and 8.3 g of 3-(p-hydroxyphenyl)-propionic acid in deionized water to make a total volume of 5 liters.

Substrate solution

A 20 mM solution of $H_2O_2$ was prepared as a substrate solution by diluting a 30% aqueous hydrogen peroxide solution with deionized water.

Labeled oligonucleotide probe solution

The same probe solution as in Example 7 was used.

Sample

The same sample as in Example 7 was used.

Use conditions of HPLC

The outline of a system was as given in FIG. 3.
Column and packing: 0.8φ×30 cm, YMC-Diol-300 (a trade name, Yamamura Chemical Laboratories Co., Ltd.).
Flow rate: the eluent; 1.0 ml/min, the substrate solution; 0.1 ml/min.
Detection: Fluorescence was measured at an excitation wavelength of 320 nm and an emission wavelength of 404 nm.

Measuring procedure

After 100 μl of the sample was heat-treated at 95° C. for 10 minutes and then ice-cooled, 100 μl of the labeled oligonucleotide probe solution was added. The resulting mixture was incubated at 37° C. for 30 minutes, after which 50 μl of the mixture was analyzed by HPLC.

Results

As a result of the analysis by HPLC, it was found that the POD-labeled oligonucleotide probe was eluted after 11.0 minutes and a complex of the POD-labeled oligonucleotide probe and the hepatitis virus B DNA after 6.5 minutes. This result indicates that HBs DNA can be detected by the process of this invention.

EXAMPLE 9

Measurement of thyroxine (T4)

Eluent

An eluent (pH 7.0) was prepared by dissolving 3.9 g of monosodium phosphate, 81 g of disodium phosphate dodecahydrate, 44 g of sodium chloride and 8.3 g of 3-(p-hydroxyphenyl)-propionic acid in deionized water to make a total volume of 5 liters.

Substrate solution

A 20 mM solution of $H_2O_2$ was prepared as a substrate solution by diluting a 30% aqueous hydrogen peroxide solution with deionized water.

Antibody solution

An antibody solution was prepared by 500-fold dilution of anti-T4 polyclonal antiserum (rabbit) (available from DAKOPATTS, Denmark) with 100 mM phosphate buffer (pH 7.0, containing 100 mM sodium chloride).

Samples

Solutions having a T4 concentration of 100, 200 or 300 μg/dl were prepared as samples by dissolving T4 in 100 mM phosphate buffer (pH 7.0, containing 100 mM sodium chloride).

Micro-POD-labeled T4 solution i) Preparation of SH group-modified micro-POD

In 40 ml of 100 mM phosphate buffer (pH 7.5, containing 100 mM sodium chloride) was dissolved 40 ml of micro-POD (hereinafter abbreviated as "MPOD": M-11, available from Sigma Chemical Co.), followed by adding thereto 2 ml of 100 mM phosphate buffer (pH 7.5, containing 100 mM sodium chloride) containing 64 mg of 3,3'-dithiobis(sulfo-succinimidyl) propionate (Pierce Chemical Co.). The reaction was carried out at 30° C. for 30 minutes. After 400 mg of ammonium acetate was dissolved in the reaction solution, the pH of the resulting solution was adjusted to 4.5 with acetic acid. Subsequently, 350 mg of dithiothreitol was added and the reaction was carried out at 30° C. for 30 minutes, after which the reaction solution was adjusted to pH 7.0 with a 4N aqueous sodium hydroxide solution and freeze-dried. The freeze-dried powder was redissolved in 2 ml of a 1N aqueous sodium hydroxide solution and purified by use of a column of BIO-GEL P-2, porous polyacrylamide beads (Bio-Rad Laboratories) equilibrated with a 50 mM aqueous ammonium acetate solution, to obtain 31 mg of SH group-modified MPOD.

ii) Preparation of MPOD-labeled T4

With 10 mg of T4 were mixed 1 ml of N,N-dimethylformamide and 1 ml of 100 mM phosphate buffer (pH 7.5, containing 100 mM sodium chloride), after which 10 mg of N-(γ-maleimidobutyryloxy)-succinimide was added. The reaction was carried out at 37° C. for 1 hour. To the reaction solution were added 5 mg of ammonium acetate and then 11 mg of the SH group-modified MPOD obtained in i) above, and the reaction was carried out at 37° C. for 2 hours, followed by purification by use of a column of BIO-GEL P-2 (mfd. by Bio-Rad Laboratories) equilibrated with a 50 mM aqueous ammonium acetate solution. Thus, 8 mg of MPOD-labeled T4 was obtained.

iii) Preparation of a MPOD-labeled T4 solution

A MPOD-labeled T4 solution was prepared by dissolving 2.2 mg of the MPOD-labeled T4 obtained in ii) above in 100 ml of 100 mM phosphate buffer (pH 7.0, containing 100 mM sodium chloride).

Use conditions of HPLC

The outline of a system was as given in FIG. 3.
Column and packing: 0.8φ×30 cm, YMC-Diol-200 (a trade name, Yamamura Chemical Laboratories Co., Ltd.).
Flow rate: the eluent; 1.0 ml/min, the substrate solution; 0.1 ml/min.
Detection: Fluorescence was measured at an excitation wavelength of 320 nm and an emission wavelength of 404 nm.

Measuring procedure

After 30 μl of each sample and 30 μl of the MPOD-labeled T4 solution were mixed, 30 μl of the antibody solution was mixed therewith at room temperature. Then, 50 μl of the resulting mixture was analyzed by HPLC.

Results

As a result of the analysis by HPLC, the following phenomenon was observed. With an increase of the T4 concentration in sample, the peak area value of free MPOD-labeled T4 was increased and that of a labeled complex of MPOD-labeled T4 and anti-T4 antibody was decreased.

Figure 9:
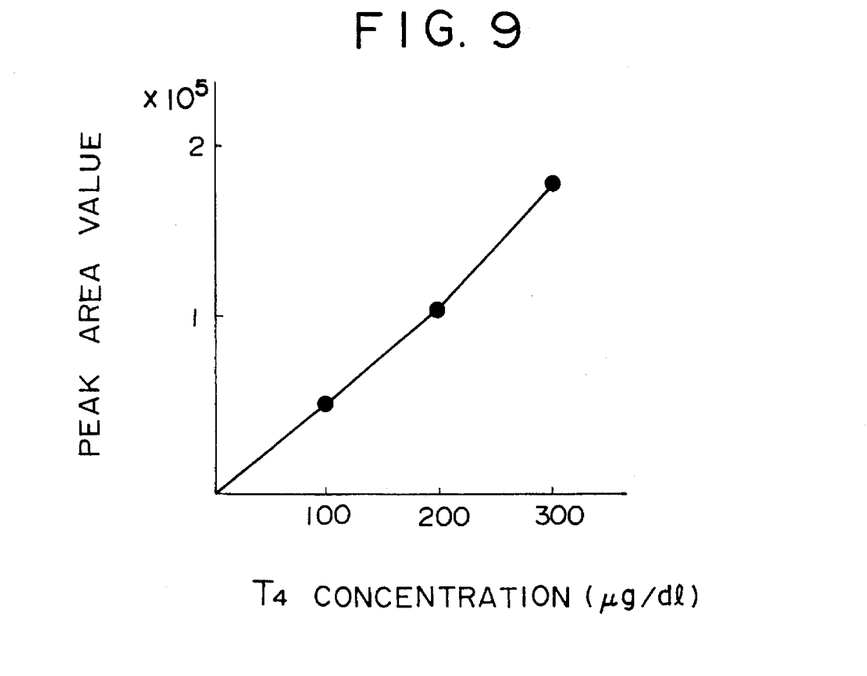
FIG. 9 shows a calibration curve for thyroxine which was obtained in Example 9.

In FIG. 9 is shown a calibration curve showing the relationship between the T4 concentration of each sample and the peak area value of free MPOD-labeled T4, which was obtained as a result of the analysis.

EXAMPLE 10

Measurement of concanabalin A-combinable POD

Eluent

An eluent was prepared by dissolving 13.0 g of monosodium phosphate, 59.7 g of disodium phosphate and 44.0 g of sodium chloride in deionized water to make a total volume of 5 liters.

Sample

A sample was prepared by dissolving POD (available from TOYOBO Co., Ltd.) in the aforesaid eluent in a concentration of 2 mg/ml.

Concanavalin A solution

A concanavalin A solution was prepared by dissolving concanavalin A (available from Wako Pure Chemical Industries, Ltd.) in the aforesaid eluent in a concentration of 3 mg/ml.

Use conditions of HPLC

Column: 0.75φ×30 cm

Packing: TSK gel G-3000 SWXL (a trade name, Tosoh Ltd.)

Flow rate: 0.7 ml/min

Detection: Absorbance at 280 nm was measured.

measuring procedure

With 60 μl of the concanavalin A solution was mixed 10 μl of the sample at room temperature, and 10 μl of the resulting mixture was analyzed by HPLC.

Results

As a result of the analysis by HPLC, it was found that concanavalin A was eluted after 16.8 minutes, POD after 14.4 minutes, and a complex of concanavalin A and POD after 8.4 minutes. This result indicates that concanavalin A-combinable POD can be detected by the process of this invention.

As described above, this invention provides a process for measuring a trace component in a sample utilizing the interaction between an analyte to be measured and a substance having affinity for the analyte (an affinity substance), in which a complex (or a labeled complex) formed by said interaction is separated from free affinity substance (or free labeled analyte) using a high pressure liquid chromatography. The process of this invention makes it possible to measure a trace component more easily in a shorter time with much higher precision as compared with conventional measuring processes according to EIA, RIA, FIA or the like which also utilize said interaction. This invention is markedly effective in this point and contributes greatly to the art.

What is claimed is:

1. A process for measuring the amount of analyte in a sample device from a living body which comprises:

mixing the sample with an affinity substance capable of binding the analyte, wherein the affinity substance is present at a concentration 5 or more times as high the concentration of the analyte corresponding to the upper limit of measurement of the analyte, and wherein the affinity substance is either labeled or unlabeled;

reacting the analyte with the affinity substance to form an analyte-affinity substance complex;

separating the analyte-affinity substance complex from free affinity substance using high pressure liquid chromatography;

directly measuring the amount of affinity substance in a fraction eluted during the high pressure liquid chromatography; and determining the amount of the analyte based upon the amount of affinity substance measured using a linear calibration curve, wherein the linear calibration curve is generated by associating known amounts of analyte with peak area values.

2. The process according to claim 1 wherein the analyte is a peptide, a nucleic acid, a chain or a lipid.

3. The process according to claim 1 wherein the analyte is an antibody and the affinity substance in an antigen, or the analyte is an antigen and the affinity substance is an antibody against the analyte.

4. The process according to claim 3 wherein the antibody against the analyte is a labeled monoclonal antibody.

5. The process according to claim 3 wherein the antibody against the analyte is labeled Fab or Fab' derived from a monoclonal antibody.

6. The process according to claim 1 wherein the analyte is a sugar chain, and the affinity substance is a lectin.

7. The process according to claim 6 wherein the lectin is concanavalin A, *Lens culinaris* lectin or *Phaseolus vulgaris* lectin.

8. The process according to claim 1 wherein the analyte is single-stranded deoxyribonucleic acid, and the affinity substance is a polynucleotide chain complementary to the single-stranded deoxyribonucleic acid.

9. The process according to claim 8 wherein the separation of the complex from free affinity substance is carried out by high pressure liquid chromatography using a column packed with hydroxyapatite.

10. The process according to claim 1 wherein the label is a fluorescent substance, a luminescent substance, a radioisotope, an enzyme, a substance which can absorb ultraviolet light, or a substance having spin properties.

11. The process according to claim 1 wherein unlabeled affinity substance is itself a substance able to emit fluorescence, a luminescent substance, an enzyme, or a substance which can absorb ultraviolet light.

12. The process according to claim 1 wherein the separation of the complex from free affinity substance is carried out by high pressure liquid chromatography using a column packed with hydroxyapatite, or packed for gel filtration, ion-exchange chromatography, hydrophobic chromatography, isoelectric focusing, or reversed phase chromatography.

13. A process for measuring the amount of analyte in a sample derived from a living body which comprises:

mixing the sample with known amount of labeled analyte and an affinity substance capable of binding the analyte to form a reaction solution, wherein the concentration of labeled analyte is not less than the concentration at which the analyte can bind to the total affinity substance present in the reaction solution;

incubating the reaction to form labeled analyte-affinity substance complex;

separating the labeled analyte-affinity substance complex from free labeled analyte using high pressure liquid chromatography;

directly measuring the amount of labeled analyte-affinity substance complex or the amount of free labeled analyte in a fraction eluted during the high pressure liquid chromatography; and determining the amount of the analyte based upon the amount of label measured using a linear calibration curve, wherein the linear calibration curve is generated by associating known amounts of analyte with peak area values.

14. The process according to claim 13 wherein the analyte is a peptide, a nucleic acid, a sugar chain or a lipid.

15. The process according to claim 13 wherein the analyte is an antibody and the affinity substance is an antigen, or the analyte is an antigen and the affinity substance is an antibody against the analyte.

16. The process according to claim 15 wherein the antibody against the analyte is a monoclonal antibody.

17. The process according to claim 15 wherein the antibody against the analyte is Fab or Fab' derived from a monoclonal antibody.

18. The process according to claim 13 wherein the label is a fluorescent substance, a luminescent substance, a radioisotope, an enzyme, a substance which can absorb ultraviolet light, or a substance having spin properties.

19. The process according to claim 13 wherein the separation of labeled complex from free labeled analyte is carried out by high pressure liquid chromatography using a column packed with hydroxyapatite, or packed for gel filtration, ion-exchange chromatography, hydrophobic chromatography, isoelectric focusing, or reversed phase chromatography.

* * * * *